(12) United States Patent
Dariush et al.

(10) Patent No.: US 7,251,593 B2
(45) Date of Patent: Jul. 31, 2007

(54) SIMULATION SYSTEM, METHOD AND COMPUTER-READABLE MEDIUM FOR HUMAN AUGMENTATION DEVICES

(75) Inventors: Behzad Dariush, Sunnyvale, CA (US); Victor Ng-Thow-Hing, San Francisco, CA (US); Darryl Gerard Thelen, Madison, WI (US)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 645 days.

(21) Appl. No.: 10/280,771

(22) Filed: Oct. 25, 2002

(65) Prior Publication Data

US 2003/0115031 A1 Jun. 19, 2003

Related U.S. Application Data

(60) Provisional application No. 60/330,689, filed on Oct. 29, 2001, provisional application No. 60/333,753, filed on Nov. 29, 2001.

(51) Int. Cl.
*G06G 7/48* (2006.01)
*G06G 7/66* (2006.01)
(52) U.S. Cl. .................. 703/11; 703/2; 703/7; 345/473; 345/474; 700/19; 700/28; 700/150; 700/247; 600/587; 600/595
(58) Field of Classification Search ................. 703/11, 703/2, 7; 345/473, 474; 700/19, 28, 30, 700/50, 247; 600/416, 587, 595
See application file for complete search history.

(56) References Cited

U.S. PATENT DOCUMENTS 4,244,120 A * 1/1981 Harris .......................... 434/59

4,786,847 A 11/1988 Daggett et al.

(Continued)

FOREIGN PATENT DOCUMENTS

JP 2000-249570 9/2000

(Continued)

OTHER PUBLICATIONS

H. Kato, and T. Hirata, "The concept of a walking assistance suit", Jun. 27, 2001, total number of pp. 20.*

(Continued)

*Primary Examiner*—Fred Ferris
*Assistant Examiner*—Kibrom K. Gebresilassie
(74) *Attorney, Agent, or Firm*—Fenwick & West LLP

(57) ABSTRACT

A system, a method and a computer readable medium are provided for simulating a combined musculoskeletal and augmentation device system. The dynamics model of the combined musculoskeletal and augmentation device system receives computed torques at the joints as inputs and delivers simulated kinematic data of the segments as outputs. The augmentation device controller for control of the augmentation device, receives the simulated kinematic data as inputs and delivers assist torques as outputs. The inverse dynamics model for the musculoskeletal and augmentation device system, receives the simulated kinematic data, desired kinematic data of the segments and the assit torques as inputs and delivers the computed net joint torque and muscle torque. The muscle force and muscle capacity module for checking and adjusting the computed torques, receives the computed torques as inputs and delivers computed torques as outputs after the checking and adjustment.

24 Claims, 9 Drawing Sheets

U.S. PATENT DOCUMENTS

| | | | |
|---|---|---|---|
| 4,834,200 A | | 5/1989 | Kajita |
| 5,044,360 A | | 9/1991 | Janke |
| 5,136,227 A | | 8/1992 | Nakano et al. |
| 5,247,432 A | * | 9/1993 | Ueda ........................... 700/42 |
| 5,362,288 A | | 11/1994 | Razon |
| 5,432,417 A | | 7/1995 | Takenaka et al. |
| 5,459,659 A | * | 10/1995 | Takenaka .................... 700/260 |
| 5,625,577 A | * | 4/1997 | Kunii et al. .................... 703/2 |
| 5,659,480 A | * | 8/1997 | Anderson et al. ........... 700/186 |
| 5,808,433 A | * | 9/1998 | Tagami et al. ......... 318/568.12 |
| 5,835,693 A | * | 11/1998 | Lynch et al. ................. 345/473 |
| 5,982,389 A | * | 11/1999 | Guenter et al. ............. 345/474 |
| 6,152,890 A | * | 11/2000 | Kupfer et al. ............... 600/595 |
| 6,161,080 A | * | 12/2000 | Aouni-Ateshian et al. .... 703/11 |
| 6,289,265 B1 | | 9/2001 | Takenaka et al. |
| 6,445,983 B1 | * | 9/2002 | Dickson et al. ............... 701/23 |
| 6,505,096 B2 | * | 1/2003 | Takenaka et al. ........... 700/245 |
| 6,580,969 B1 | | 6/2003 | Ishida et al. |
| 6,633,783 B1 | * | 10/2003 | Dariush et al. ............... 700/50 |
| 6,640,160 B2 | * | 10/2003 | Takahashi et al. .......... 700/245 |
| 6,750,866 B1 | * | 6/2004 | Anderson, III ............. 345/474 |
| 6,766,204 B2 | * | 7/2004 | Niemeyer et al. ............. 700/1 |
| 6,785,591 B1 | * | 8/2004 | Hansson ..................... 700/275 |
| 6,943,520 B2 | * | 9/2005 | Furuta et al. .......... 318/568.12 |
| 7,013,201 B2 | * | 3/2006 | Hattori et al. ............... 700/245 |
| 7,135,003 B2 | * | 11/2006 | Dariush ....................... 600/595 |
| 2003/0018283 A1 | * | 1/2003 | Dariush ....................... 600/595 |
| 2003/0023415 A1 | * | 1/2003 | Nakamura et al. ............. 703/2 |
| 2004/0102723 A1 | | 5/2004 | Horst |
| 2004/0107780 A1 | * | 6/2004 | Kawai et al. ............ 73/862.08 |
| 2004/0158175 A1 | | 8/2004 | Ikeuchi et al. |
| 2004/0249319 A1 | | 12/2004 | Darlush |
| 2004/0254771 A1 | * | 12/2004 | Riener et al. ................... 703/7 |
| 2005/0102111 A1 | | 5/2005 | Dariush et al. |
| 2005/0104548 A1 | | 5/2005 | Takenaka et al. |
| 2005/0209535 A1 | * | 9/2005 | Dariush ....................... 600/595 |
| 2006/0046909 A1 | * | 3/2006 | Rastegar et al. ............. 482/91 |
| 2006/0100818 A1 | * | 5/2006 | Nakamura et al. .......... 702/142 |
| 2006/0139355 A1 | * | 6/2006 | Tak et al. .................... 345/473 |

FOREIGN PATENT DOCUMENTS

| | | |
|---|---|---|
| RU | 2 107 328 C1 | 3/1998 |
| WO | WO 00/35346 | 6/2000 |

OTHER PUBLICATIONS

Hisashi Kato, and Takashi Hirata. "The Concept of a walking assistance suit." Jun. 2001.*
Paul M. Isaacs, and Michael F. Cohen. "Controlling Dynamic Simulation with Kinematic Constraints, Behavior Functions, and Inverse Dynamics". Computer Graphics, vol. 21, No. 4, Jul. 1987.*
U.S. Appl. No. 60/300,815, filed Jun. 27, 2001, "The Concept of a Walking Assistance Suite", Kato, Hisashi, et al., "The Concept of a Walking Assistance Suit, Welfare Engineering Symposium", The Japan Society of Mechanical Engineers, Aug. 2001.
Bronzino, Joseph D., "The Biomedical Engineering Handbook", IEEE Press, 2$^{nd}$ Ed. vol. 2, 2000, Chapter 142, pp. 1-17.
Agarwal, S.K. et al., "Theory and Design of an Orthotic Device for Full or Partial Gravity-Balancing of a Human Leg During Motion," IEEE Transactions on Neural Systems and Rehabilitation Engineering, Jun. 2004, vol. 12, No. 2.
Akhlaghi, F. et al., "In-shoe Biaxial Shear Force Measurement: the Kent Shear System," Medical & Biological Engineering & Computing, Jul. 1996, vol. 34, pp. 315-317.
Anderson, F. et al., "Dynamic Optimization of Human Walking," Journal of Biomechanical Engineering, Oct. 2001, vol. 123, pp. 381-390.
Anderssen, R. et al., "Numerical Differentiation Procedures for Non-Exact Data," Numereische Mathematik, 1974, vol. 22, pp. 157-182.
Baruh, H., Analytical *Dynamics*, Chapter 7, Rigid Body Kinematics, McGraw-Hill, 1999, pp. 355-371.
Blaya, J., "Force-Controllable Ankle Foot Orthosis (AFO) to Assist Drop Foot Gait," Feb. 2003, web.mit.edu/jblaya/www/MSthesis_final.pdf.
Burdea, G. et al., "Virtual Reality Technology", 1994, pp. 33-37, John Wiley and Sons, Inc.
Busby, H.R. et al., "Numerical Experiments With a New Differentiation Filter," Transactions of the ASME—Journal of Biomechanical Engineering, Nov. 1985, vol. 107, pp. 293-299.
Chao, E.Y. et al., "Application of Optimization Principles in Determining the Applied Moments in Human Leg Joints During Gait," J. Biomechanics, 1973, vol. 6, pp. 497-510, Pergamon Press, Great Britain.
Craig, J.J., "Nonlinear Control of Manipulators," Introduction to Robotics Mechanics and Control, 2$^{nd}$, Ed., 1989, Chapter 10, pp. 333-361.
Crowninshield, R.D. et al., "A Physiologically Based Criterion Of Muscle Force Prediction In Locomotion," *Journal of Biomechanics*, vol. 14, No. 11, 1981, pp. 793-801.
Cullum, J., "Numerical Differentiation and Regularization," SIAM J. Numer. Anal., Jun. 1971, vol. 8, No. 2, pp. 254-265.
Dariush, B. et al., "Multi-Modal Analysis of Human Motion From External Measurements," Transactions of the ASME, Jun. 2001, vol. 123, pp. 272-278.
Dariush, B, "A Novel Algorithm For Generating A Forward Dynamics Solution To The Traditional Inverse Dynamics Problem," In *4th World Congress of Biomechanics*, Calgary, Canada, 2002.
Dariush, B., "A Forward Dynamics Solutions To Multi-Modal Inverse Dynamics Problems," in *International Society of Biomechanics, XIXth Congress*, Dunedin, NZ, 2003.
Dariush, B., "A Well-Posed, Embedded Constraint Representation of Joint Moments From Kinesiological Measurements," Journal of Biomechanical Engineering, Aug. 2000, vol. 122, pp. 437-445.
Delp, S. et al., "A Computational Framework for Simulating and Analyzing Human and Animal Movement," *IEEE Computing in Science and Engineering*, vol. 2, No. 5, 2000; pp. 46-55.
Dohrmann, C.R. et al., "Smoothing Noisy Data Using Dynamic Programming and Generalized Cross-Validation" Transactions of the ASME—Journal of Biomechanical Engineering, Feb. 1988, vol. 110, pp. 37-41.
Gagnon, D. et al., "The Influence of Dynamic Factors on Triaxial Net Muscular Moments at the L5/S1 Joint During Asymmetrical Lifting and Lowering", Journal of Biomechanics, vol. 25, pp. 891-901, 1992.
Gagnon, M. et al., "Muscular Mechanical Energy Expenditure as a Process for Detecting Potential Risks in Manual Materials Handling," J. Biomech., Nov. 1991, pp. 191-203, vol. 24, No. 3/ 4.
Giakas, G. et al., "A Comparison of Automatic Filtering Techniques Applied to Biomechanical Walking Data," J. Biomechanics 1997, vol. 00, No. 00, 4 pages.
Giakas, G. et al., "Optimal Digital Filtering Requires a Different Cut-Off Frequency Strategy for the Determination of the Higher Derivatives," J. Biomechanics, Apr. 1997, vol. 28, No. 00, 5 pages.
Grood, E.S. et al., "A Joint Coordinate System for the Clinical Description of Three Dimensional Motions: Application to the Knee," Journal of Biomechanical Engineering, 1983, pp. 136-144, No. 105.
Hatze, H. "The Use of Optimally Regularized Fourier Series for Estimating Higher-Order Derivatives of Noisy Biomechanical Data," J. Biomechanics, 1981, vol. 14, pp. 13-18.
Hayashibara, Y. et al., "Design of a Power Assist System with Consideration of Actuator's Maximum Torque," 4$^{th}$ IEEE International Workshop on Robot and Human Communication, RO-MAN'95, Tokyo, Jul. 5-7, 1995, pp. 379-384, [online] Retrieved from the Internet<URL:http://ieeexplore.ieee.org/xpl/abs_free.jsp?arNumber=531990>.
Hemami, H. et al., "Modeling And Control Of Constrained Dynamic Systems With Application To Biped Locomotion In The Frontal Plane," *IEEE Transactions on Automatic Control*, vol. 4, No. 4, Aug. 1979, pp. 526-535.

Hemami, H., "A State Space Model for Interconnected Rigid Bodies," IEEE Trans. on Automatic Control, 1982, pp. 376-382, vol. 27, No. 2.

Hosein, R. et al., "A Study of in-shoe Plantar Shear in Normals," Clinical Biomechanics, 2000, vol. 15, pp. 46-53.

Hsiang, S.H. et al., "Three Different Lifting Strategies for Controlling the Motion Patterns of the External Load", Ergonomics, vol. 40, pp. 928-939, 1997.

Jalics, L. et al., "A Control Strategy for Terrain Adaptive Bipedal Locomotion," Autonomous Robots, 1997, pp. 243-257, vol. 4.

Jezernk, S. et al., "Robotic Orthosis Lokomal: A Rehabilitation and Research Tool," Neuromodulation, 2003, pp. 108-115, vol. 6, No. 2.

Kato, H. et al., "The Concept of a Walking Assistance Suit", The Japanese Society of Mechanical Engineers, Aug. 2001.

Kawato, M., "Internal Models for Motor Control and Trajectory Planning," Current Opinion in Neurobiology, 1999, pp. 718-727, No. 9.

Khatib, O., A Unified Approach For Motion And Force Control Of Robot Manipulators: The Operational Space Formulation, *IEEE Journal of Robotics and Automation*, RA-3(1), 1987, pp. 43-53.

Klein, C. A. et al., Review Of Pseudoinverse Control For Use With Kinematically Redundant Manipulators, *IEEE Transactions on Systems, Man, and Cybernetics*, vol. 13, No. 2, 1983, pp. 245-250.

Park, J.H. et al., Biped Robot Walking Using Gravity-Compensated Inverted Pendulum Mode and Computed Torque Control, 1998 IEEE Conference on Robotics and Automation, May 16-20, 1998, pp. 2528-2533, vol. 4, [online] Retrieved from the Internet<URL:http://ieeexplore.ieee.org/xpl/abs_free.jsp?arNumber=680985>.

Piazza, S. et al., "Three-Dimensional Dynamic Simulation of Total Knee Replacement Motion During a Step-up Task," *Journal of Biomechanical Engineering*, vol. 123, 2001, pp. 599-606.

Rahman, T. et al., "A Simple Technique to Passively Gravity-Balance Articulated Mechanisms," Journal of Mechanical Design, 1995, pp. 655-658, vol. 117, No. 4.

Runge, C.F. et al., "Estimating Net Joint Torques From Kinesiological Data Using Optimal Linear System Theory." IEEE Transactions on Biomedical Engineering, Dec. 1995, vol. 42, No. 12, pp. 1158-1164.

Shadmehr, R. et al., "Interference in Learning Internal Models of Inverse Dynamics in Humans," Advances in Neural Information Processing Systems, 1995, pp. 1117-1224, Chapter 7.

Simons, W. et al., "Differentiation of Human Motion Data Using Combined Spline and Least Squares Concepts," Journal of Biomechanical Engineering, Transactions of the ASME, Aug. 1991, vol. 113, pp. 348-351.

Thelen, D. et al., "Generating Dynamic Simulations of Movement Using Computed Muscle Control," *Journal of Biomechanics*, 36, 2003, pp. 321-328.

Transmittal of the International Search Report, PCT/US02/20829, Dec. 12, 2002, 4 pages.

"Unsupported Standing with Minimized Ankle Muscle Fatigue," [online] Retrieved from the Internet<URL:http://ieeexplore.ieee.org/iel5/10/29163/01315854.pdf>, Aug. 2004.

Vaughan, C. L. et al., "Appendix B., Detailed Mathematics Used in GaitLab," *Dynamics of Human Gait*, Second Edition, Kiboho Publishers, Cape Town South Africa, 1999, pp. 83-106.

Vukobratovic, M. et al., *Scientific Fundamentals of Robotics 7: Biped Loco-motion*. Springer-Verlag, 1990, pp. 17-27.

Wells, R. et al., "Internal and Physiological Responses During Concentric and Eccentric Cycle Ergometry," Eur. J. Appl. Physiol., 1986, pp. 291-301, vol. 55.

Winter, D.A., "Biomechanics and Motor Control of Human Movement", 2nd Edition, John Wiley & Sons, Inc., pp. 51-74, 1990.

Winter, D.A., "Kinetics: Forces and Moments of Force," Biomechanics and Motor Control of Human Movement, 2nd Ed., New York, 1990, Chapter 4.

Wittenberg, J., *Dynamics of Systems of Rigid Bodies*, 1977, B.G. Teubner Stuttgart, 1977, pp. 29-30.

Woltring, H.J., "A Fortran Package for Generalized, Cross Validatory Spline Smoothing and Differentiation," Adv. Eng. Software, 1986, vol. 8, No. 2, pp. 104-107.

Woltring, H.J., "On Optimal Smoothing and Derivative Estimation From Noisy Displacement Data in Biomechanics," Human Movement Science, vol. 4, 1985, pp. 229-245.

Written Opinion, PCT/IB02/04311, Feb. 20, 2003, 2 pages.

Gruber, K., et al., "A Comparative Study of Impact Dynamics: Wobbling Mass Model Versus Rigid Body Models", Journal of Biomechanics, 31 (1998), pp. 439-444.

Hemami, H., "A Feedback On-Off Model of Biped Dynamics", IEEE Transactions on Systems, Men, and Cybernetics, Jul. 1980, vol. SMC-10, No. 7, pp. 376-383.

Wolpert, D.M., et al., "Ocular Limit Cycles Induced by Delayed Retinal Feedback", Experimental Brain Research, 1993, vol. 96, pp. 173-180.

Flanagan, Randall J., et al., "The Role of Internal Models in Motion Planning and Control Evidence from Grip Force Adjustments During Movements of Hand-Held Loads", The Journal of Neuroscience, Feb. 15, 1997, vol. 17(4), pp. 1519-1528.

Atkeson, Christopher G., "Learning Arm Kinematics and Dynamics", Annual Reviews, Inc., 1989, vol. 12, pp. 157-183.

Kawato, Mitsuo, "Adapation and Learning in Control of Voluntary Movement by the Central Nervous System", 1989, Advanced Robotics, vol. 3, pp. 229-249.

Shadmehr, R., "Learning Virtual Equilibrium Trajectories for Control of a Robot Arm", Neural Computation, 1990, vol. 2, pp. 436-446.

Kawato Mitsuo, et al., "The Cerebellum and VOR/OKR Learning Models", Elsevier Science Publishers Ltd., 1992, vol. 15, No. 11, pp. 445-453.

Anderson, Frank C., "Static and Dynamic Optimization Solutions for Gait are Practically Equivalent", Journal of Biomechancis, 2001, vol. 34, pp. 153-161.

Zajac, Felix E., "Muscle and Tendon Properties, Models, Scaling, and Application to Biomechancis and Motor Control", 1989, vol. 17, Issue 4, pp. 359-411.

Hungspreugs, Pinata, et al., "Muscle Force Distribution Estimation Using Static Optimization Techniques", Technical Report—Honda R&D Americas, Apr. 2001.

International Search Report and Written Opinion, PCT/US06/11727, Nov. 9, 2006 9 pages.

* cited by examiner

SIMULATION SYSTEM, METHOD AND COMPUTER-READABLE MEDIUM FOR HUMAN AUGMENTATION DEVICES

CROSS-REFERENCE TO RELATED APPLICATIONS

This application claims priority of U.S. provisional applications No. 60/330,689 filed on Oct. 29, 2001 and No. 60/333,753 filed on Nov. 29, 2001.

FIELD OF THE INVENTION

The present invention relates to a simulation system, a simulation method and a computer-readable medium for analysis, and synthesis of human motion under partial assist from powered augmentation devices.

BACKGROUND OF THE INVENTION

Effective usage of human assistive systems or augmentation devices for restoration or enhancement of motor function is an important area of research in rehabilitation and performance enhancement. A partial list of important and desired features of an effective assistive system include: (1) a decrease in energy rate and cost with respect to able-bodied subjects performing the same task, (2) minimum disruption and maximum comfort of normal activities when employing the assistive system, and (3) practicality. The third requirement considers the ease of wearing such a device and its power consumption needs. These requirements and available technology have led to the development of externally powered orthoses and prostheses that interface directly or indirectly with the human neuromuscular system. Although significant progress has been made in meeting many of the requirements needed for development of practical human assist devices (Popovic, D., Externally Powered and Controlled Orthotics and Prosthetics. The Biomedical Engineering Handbook, Editor Bronzino, J. D., 2nd ed. Vol. 2, Chapter 142, 2000), realization of such systems for daily applications is still in its infancy. The complexity of the central nervous system (CNS) control and the interface between voluntary control and external artificial control are still challenging, unanswered questions.

At Honda's Wako Research Center, a mechanically powered walking assist prototype system was recently unveiled (Katoh and Hirata, The Concept of a Walking Assistance Suit, Welfare Engineering Symposium, The Japan Society of Mechanical Engineers, August 2001). The target application is to help the elderly and disabled people to either execute daily tasks they could not previously perform, or use less physical exertion than they currently employ for these tasks. The tasks considered include walking, lifting, sitting/standing, and climbing stairs. Two important and challenging questions to consider in the implementation of the Honda prototype and similar human augmentation systems include: 1) analysis and monitoring of biomechanical as well as physiological quantities which cannot be readily measured and 2) the synthesis of an active control which can safely and effectively augment voluntary control. By developing computational methods to study these issues, future performance of human augmentation devices can be studied through simulation, without constraints imposed by hardware implementations of current technology. Simulation studies also enable us to estimate physiological quantities that cannot be easily measured, including muscle forces, joint forces, and energetics of motion. We can simulate effects of aging, predict muscular activity, estimate muscle fatigue and capacity, and detect potential dangerous physiological conditions. It should be mentioned that the exclusive use of simulation is not a substitute for eventual testing on live human subjects. However, an accurate subject-specific simulation allows control algorithms to be designed and refined for the walking assist device. This is especially relevant in our target user population because they already have existing health constraints.

U.S. Pat. No. 6,152,890 discloses a device and a method for the recording, presentation and automatic classification of biomechanical variables measured on a freely moving test person during a work shift.

Japanese patent publication unexamined No. 2000-249570 discloses a method for generating human kinematic data.

"Gruber, K. et. al., 1998. A comparative study of impact dynamics: wobbling mass model versus rigid body models. Journal of Biomechanics 31, 439–444" discloses inverse dynamics model used to simulate the human body.

However, any of the above documents does not deal with analysis and synthesis of human motion under assist from powered augmentation devices.

Accordingly, what is needed is a system and a method for analysis and synthesis of human motion under assist from powered augmentation devices.

SUMMARY OF THE INVENTION

According to one aspect of the invention, a simulation system is provided for a combined musculoskeletal and augmentation device system including segments and joints connecting the segments. The simulation system comprises a dynamics model of the combined musculoskeletal and augmentation device system and an augmentation device controller for control of the augmentation device. The simulation system further comprises an inverse dynamics model for the musculoskeletal and augmentation device system and a muscle force and muscle capacity module for checking and adjusting the computed torques. The dynamics model of the combined musculoskeletal and augmentation device system receives feasible computed torques at the joints as inputs and delivers simulated kinematic data of the segments as outputs. The augmentation device controller for control of the augmentation device, receives the simulated kinematic data as inputs and delivers assist torques as outputs. The inverse dynamics model for the musculoskeletal and augmentation device system, receives the simulated kinematic data, desired kinematic data of the segments and the assist torques as inputs and delivers the computed muscle torques and net joint torque as outputs. The muscle force and muscle capacity module for checking and adjusting the computed torques, receives the computed muscle torques as inputs and delivers feasible computed torques as outputs after making adjustments to the computed torques.

According to another aspect of the invention, a method is provided for simulating a combined musculoskeletal and augmentation device system including segments and joints connecting the segments. The method comprises the steps of computing assist torques of the augmentation device, based on simulated kinematic data and computing torques based on the simulated kinematic data, desired kinematic data of the segments and the assist torques. The method further comprises the steps of checking and adjusting the computed torques and computing the simulated kinematic data of the segments based on the computed torques at the joints.

According to another aspect of the invention, a computer readable medium containing a program for simulating a combined musculoskeletal and augmentation device system including segments and joints connecting the segments, is provided. The program comprises instructions of computing assist torques of the augmentation device, based on simulated kinematic data and of computing torques based on the simulated kinematic data, desired kinematic data of the segments, and the assist torques. The program further comprises instructions of checking and adjusting the computed torques and of computing the simulated kinematic data of the segments based on computed torques at the joints.

According to an embodiment of the invention, muscle forces are deduced from the computed torques, compared with maximum force limits and adjusted if the muscle forces exceed limits, to obtain feasible torques.

According to another embodiment of the invention, muscle forces with and without the assist torques are compared in order to asses whether the assist torque control helps or hinders motion and if the assist torque control hinders motion the muscle forces are adjusted and feasible joint torques are computed.

According to another embodiment of the invention, muscle forces with and without the assist torques are compared in order to asses whether the assist torque control helps or hinders motion and if the assist torque control hinders motion the assist torque control law is adjusted to ensure that feasible joint torques are computed.

According to another embodiment of the invention, muscle forces are deduced based on a static optimization criterion in which a sum of muscle activation squared is minimized.

According to another embodiment of the invention, modified accelerations of kinematic data are obtained through non-linear position and velocity feedback from the simulated kinematic data.

According to another embodiment of the invention, the kinematic data include position data, velocity data and acceleration data and estimates of kinematic data are computed, through non-linear feedback based on desired acceleration data, error between simulated position data and desired position data and error between simulated velocity data and desired velocity data.

According to another embodiment of the invention, the kinematic data include position data, velocity data and acceleration data and estimates of kinematic data are computed, through non-linear feedback based on error between simulated position data and desired position data and/or error between simulated velocity data and desired velocity data.

According to another embodiment of the invention, computed reaction forces under the segments contacting the ground are obtained based on the feasible computed torques and the simulated kinematic data.

According to another embodiment of the invention, gravity compensation control algorithm is employed, in which the assist torques are obtained to reduce the computed muscle force by artificially compensating for the forces due to gravity.

According to another embodiment of the invention, change in the computed torques, due to compensation for gravity is obtained, using coordinates of the center of the mass of the segments.

According to another embodiment of the invention, the coordinates of the center of the mass of the segments, are obtained from measurements of joint angles and segment lengths.

According to another embodiment of the invention, change in the computed torques, due to compensation for gravity, is obtained using measured reaction forces under the feet.

According to another embodiment of the invention, the feedback gains are selected to produce the fastest possible non-oscillatory response.

DETAILED DESCRIPTION OF THE PREFERRED EMBODIMENTS

The present invention provides computational methods for analysis, and synthesis of human motion under partial assist from powered augmentation devices. The algorithms are integrated in a simulation platform to be used as a test-bed for prototyping, simulating, and verifying algorithms to control human motion under artificial control. The analysis and synthesis problems in human motion are formulated as a trajectory tracking control algorithm using inverse and forward models coupled by proportional and derivative feedback terms. A muscle force distribution and capacity module is used to monitor the computed joint torques in order to assess the physiological consequences of the artificial control, and if needed to make modifications. This framework allows us to verify robustness, stability, and performance of the controller, and to be able to quickly change parameters in a simulation environment. We can study many different motions in a simulation environment. Thus, future performance and designs of human augmentation devices can be studied through simulation, without the risk and constraints imposed by hardware implementations of current technology.

The System Model

Figure 1:
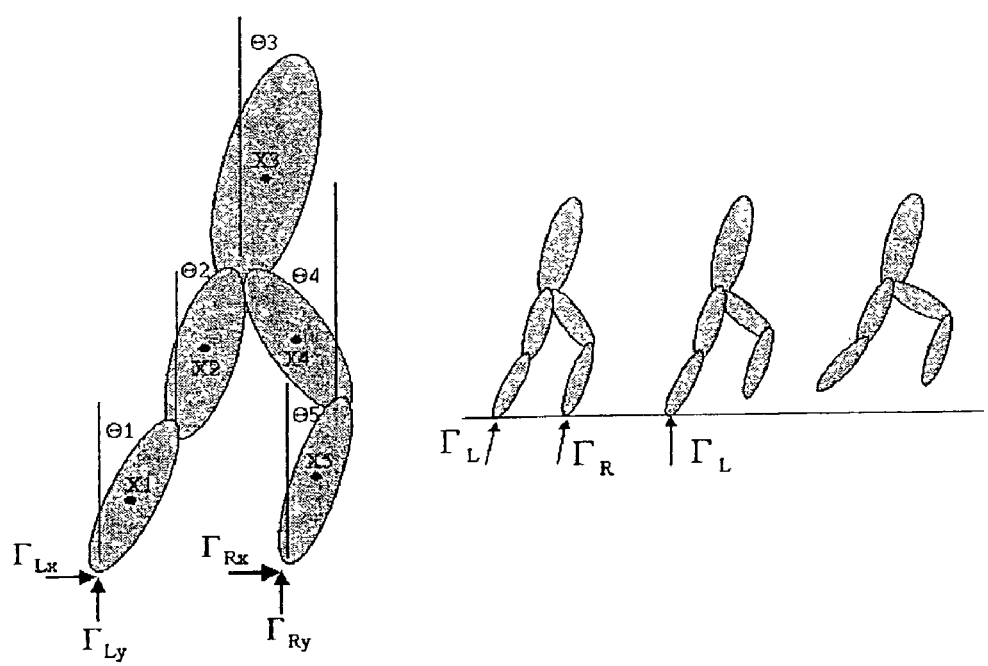
FIG. 1 a biped system having five degrees of freedom in the sagittal plane with intermittent ground contact during double support, single support, and air-born phase.

The system (or plant) refers to a dynamic model of the combined musculoskeletal and augmentation device system. The system may be designed having various degrees of complexity, depending on the requirements imposed by the study. Without loss of generality, we consider a simple planar biped system to illustrate the concepts (See FIG. 1). The equations of motion are formulated in such a way to handle three phases of biped motion as shown in FIG. 1. They include single support, double support, and airborn. Let q be the coordinates corresponding to the rotational and translational degrees of freedom.

$$q = [x_3 y_3 \Theta_1 \Theta_2 \Theta_3 \Theta_4 \Theta_5]^T \quad (1)$$

where $(x_3, y_3)$ corresponds to the center of mass of the torso and the joint angles $\Theta$ are measured clockwise from the vertical.

The system is actuated by voluntary control from the muscles and artificial control from the augmentation device. The total torque applied at the joints (net joint torque) are the combined torque from the muscles ($\tau_m$) and the assist actuators ($\tau_a$)

$$\tau = \tau_a + \tau_m \quad (2)$$

Let $C(q)$ represent the foot-floor contact constraints and $\Gamma = [\Gamma_L^T \Gamma_R^T]^T$ be the vector corresponding to the ground reaction forces under the left and right feet. The equations of motion of the system are given by, $$J(q)\ddot{q} + B(q, \dot{q})\dot{q} + G(q) + T_{ad} = \frac{\partial C^T}{\partial q}\Gamma' + D\tau \quad (3)$$

where J, B, and G correspond to the inertia, coriolis and centrifugal torques, and gravitational terms, respectively. The vector $T_{ad}$ models the augmentation device dynamics and the constant matrix D characterizes the torque coupling effects at the joints. The matrix D is present because absolute coordinates for the joint angles are used in the formulation of the equation of motion, as opposed to relative coordinates. The ground reaction forces may be expressed as a function of the state and inputs by (Hemami, H., A feedback On-Off Model of Biped Dynamics. IEEE Transactions on Systems, Man, and Cybernetics, Vol. SMC-10, No. 7, July 1980).

$$\Gamma = \left(\frac{\partial C}{\partial q} J(q)^{-1} \frac{\partial C^T}{\partial q}\right)^{-1} \left(-\frac{\partial}{\partial q}\left(\frac{\partial C}{\partial q}\dot{q}\right)\dot{q} + \frac{\partial C}{\partial q} J(q)^{-1}(B(q, \dot{q})\dot{q} + G(q) + T_{ad} - D\tau)\right) \quad (4)$$

Figure 2:
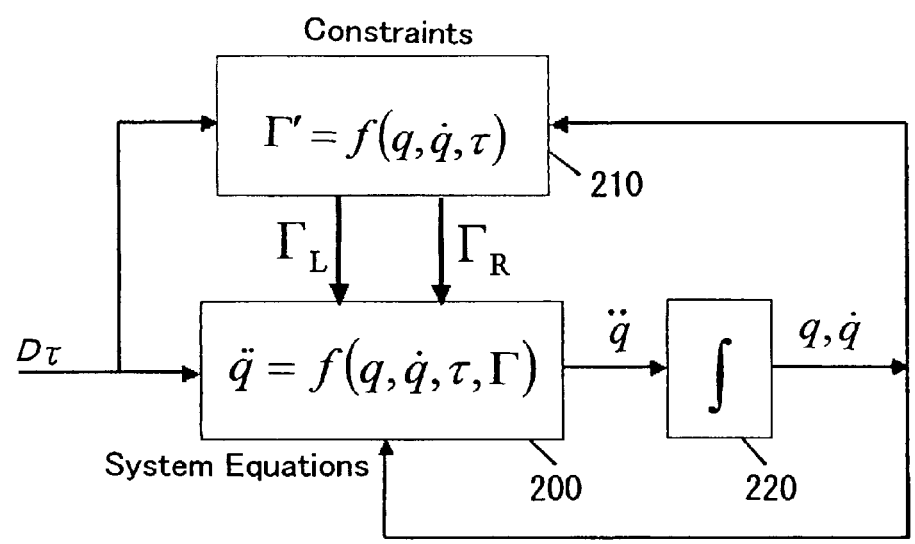
FIG. 2 is a system model description with intermittent contact of left and right feet with the ground.

FIG. 2 shows a system model description with intermittent contact of left and right feet with the ground. Forward dynamic simulations are performed by computing the induced accelerations $\ddot{q}$ obtained from Equation 3 and Equation 4, using the simulated state variable q and $\dot{q}$ which are obtained by numerical integration.

The Internal (Inverse) Model

It has been demonstrated that the behavior of the human body when coupled with a novel mechanical system is very similar to the behavior that results when the controller relies on an internal model. One such internal model is thought to be a forward model, a term used to describe the computations involved in predicting sensory consequences of a motor command. There are a number of studies that have suggested that a forward model may be used by the human central nervous system (CNS) to estimate sensory consequences of motor actions (Wolpert, D. M., Miall, R. C., Kerr, G. K., Stein, J. F. Ocular limit cycles induced by delayed retinal feedback. Exp Brain Res., 96: 173–180, 1993; Flanagan. J. R., Wing, A. M. The role of internal models in motion planning and control: evidence from grip force adjustment during movements of hand held loads. J. Neurosci, 17:1519–1528, 1997). This theory is easily understood when considering transmission delays inherent in the sensory-motor loop. Although a forward model is particularly relevant to feedback control of time delayed systems, an inverse model is sometimes considered to predict the motor commands that are appropriate for a desired behavior (Atkeson, C. G. Learning arm kinematics and dynamics. Annu Rev. Neurosci, 12:157–183, 1989; Kawato, M., Adaptation and learning in control of voluntary movement by the central nervous system. Advanced Robotics 3, 229–249, 1989; Shadmehr, R., Learning virtual equilibrium trajectories for control of a robot arm. Neural Comput, 2:436–477, 1990; Gomi, H., Kawato, M., The cerebellum and vor/okr learning models. Trends Neurosci, 15:445–453, 1992).

Figure 3:
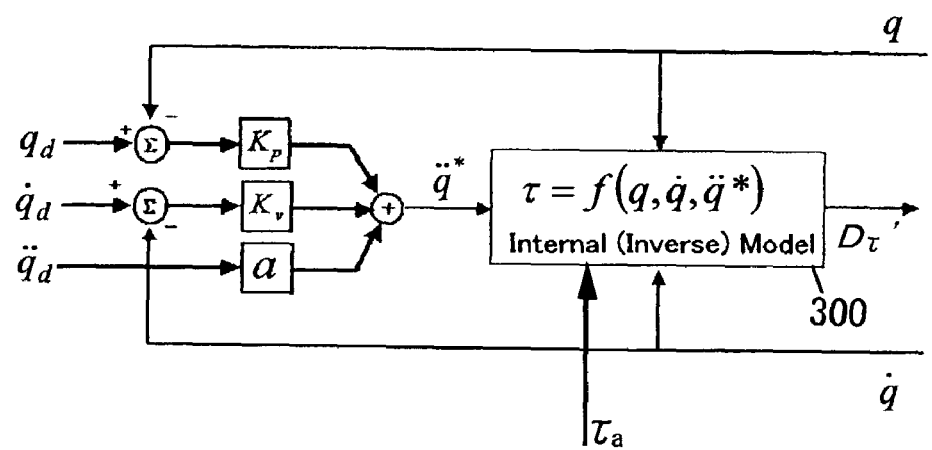
FIG. 3 is an inverse dynamics controller with position and velocity feedback for calculation of torques that when applied to a system model, will track and reproduce the desired kinematic data.

Inverse models are generally not considered for control of time delayed systems since the controller would seem to not have the ability to respond to the error and results in instability. However, it is plausible that local or intrinsic feedback mechanisms in conjunction with an inverse model can function to stabilize a system with latencies. Local feedback with stabilizing characteristics is believed to exist in humans in the form of viscoelastic properties of muscles and spinal reflex loop. The concept of an inverse model is also attractive for analysis problems of biomechanical quantities, whereby internal loads are estimated from kinesiological measurements. The approach adopted here in developing a computational model of human sensory motor control is based on the concept of an inverse model coupled with nonlinear feedback (FIG. 3). This mechanism is compelling from the standpoint of biomechanical analysis of human motion as well as the synthesis of artificial control. Let $q_d$ represent the desired kinematics, obtained from motion capture data. The following control law ($D\tau'$), when applied to the system equations, will result in a simulated response that will track and reproduce the desired kinematics data, $$D\tau' = J(q)\ddot{q}^* + B(q, \dot{q})\dot{q} + G(q) + T_{ad} - \frac{\partial C^T}{\partial q}\Gamma' \quad (5)$$

where, $$\ddot{q}^* = a\ddot{q}_d + K_p(q_d - q) + K_v(\dot{q}_d - \dot{q}) \quad (6)$$

The diagonal matrices $K_p$ and $K_v$ represent the position and velocity feedback gains, respectively. The eigenvalues of the closed loop system are related to the feedback gains by the following, $$K_p = -(\lambda_1 + \lambda_2) \quad (7)$$

$$K_v = \lambda_1 \lambda_2 \quad (8)$$

A critically damped response (fastest possible non-oscillatory response) to the tracking error can be achieved by specifying the eigenvalues to be equal, real, and negative.

The parameter a is constant and set to 0 or 1, depending on the severity of noise in the measurements. If the desired trajectories are obtained from noisy motion capture measurements, it may be appropriate to set a=0 and to specify the eigenvalues to be large and negative. This way, tracking is achieved without the need to compute unreliable accelerations from noisy kinematics data.

Muscle Force and Muscle Capacity

Figure 5:
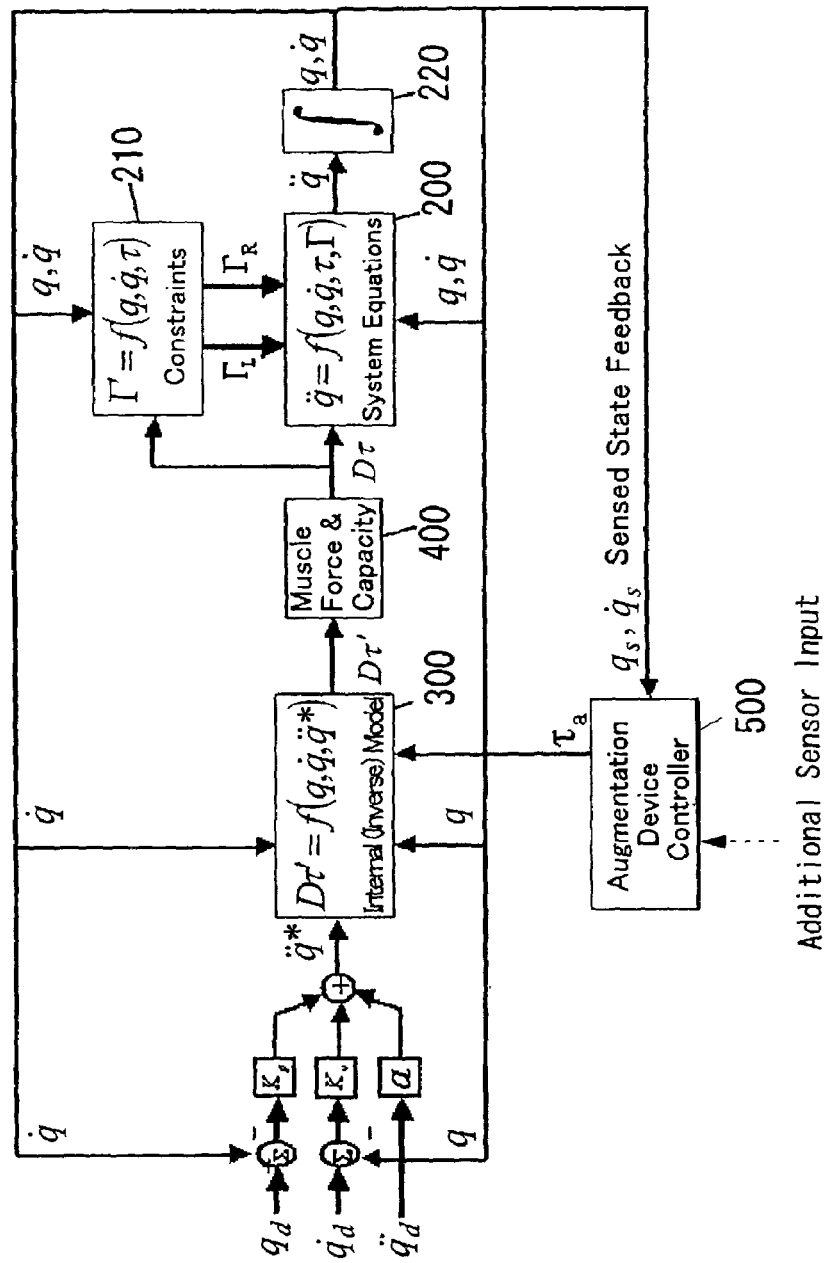
FIG. 5 is a block-diagram of the integrated simulation system.

The muscle force and muscle capacity module should ideally be implemented in the forward path of the closed loop system (as shown in FIG. 5). However, it may also be implemented as a separate module whose output is used for analysis purpose only. In the latter case, the module's inputs would tap into the required variables of the closed loop system, but the module would not alter the closed loop dynamics.

In either case, a number of different muscle force distribution algorithms may be implemented. The underlying concepts of our choice of muscle force distribution algorithm is presented below.

The relationship between the net muscular moment $\tau_m$ and the muscle forces $F_m$ is given by, $$D\tau_m = -\frac{\partial L^T}{\partial q} F_m \quad (9)$$

where L is the overall length of the muscle actuator, and $\partial L^T/\partial q$ is an (n×m) muscle moment arm matrix. Since the number of muscles (m) exceeds the degrees of freedom (n), the computation of the muscle actuator's excitation inputs (and the resulting forces) from an inverse dynamics computation amounts to solving a problem that is inherently ill-posed. Static, nonlinear optimization has been used extensively to predict the individual muscle forces to produce the required torque. There are several compelling reasons for using static optimization to predict the individual muscle forces: first, static, non-linear optimization techniques have well developed theoretical foundations. With the advance of commercial software for solving general, constrained, multi-variable non-linear optimization problems, it is now possible to solve sophisticated problems numerically in relatively short time. Second, the notion that muscle forces are controlled in some way to optimize physiological criteria has great intuitive appeal. It has been shown that for motions like walking, static optimization yields very similar results to dynamic optimization (Anderson, F C and Pandy, M G., Static and Dynamic Optimization Solutions for Gait are practically equivalent, Journal of Biomechanics 34, 2001, 153–161, 2001).

Figure 4:
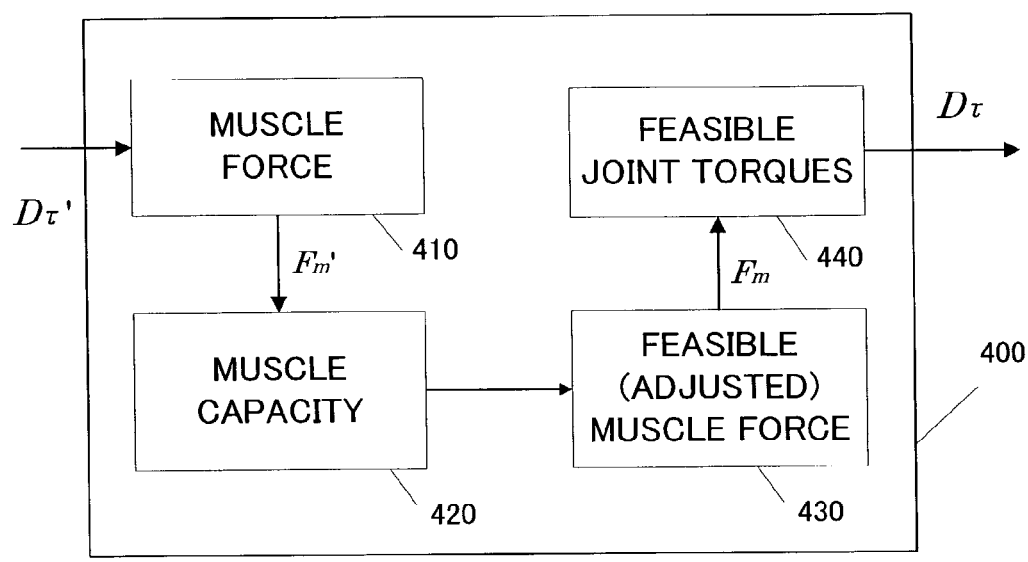
FIG. 4 is a muscle force and muscle capacity module.

A muscle force and muscle capacity module takes the computed torques from the inverse model (denoted by $D\tau'$) as inputs and calculates the muscle forces based on a static optimization criterion (module 410 in FIG. 4). While any cost function can be defined in solving the optimization problem, the one used here minimizes the sum of muscle activations squared $$J = \sum_{i=1}^{m} a_i^2 \quad (10)$$

where m is the number of muscles crossing the joint, $a_i$ is the activation level for muscle i and is constrained to be between 0.01 and 1.0. A muscle force $F_i$ for muscle i can be represented as below;

$$F_i = a_i F_i^0 \quad (11)$$

where $$F_i^0$$

represents a maximum force limit for muscle i. A gradient based technique can be used to numerically solve for the muscle activations that minimize the cost function J while satisfying the joint moment equilibrium for all degrees of freedom of interest. The optimization problem can be solved using constrained nonlinear optimization (Sequential Quadratic Programming; AEM Design). Once the muscle activations are obtained, the muscle force can then be determined using the force-length-velocity-activation relationship of muscle (Zajac, F. E. Muscle and tendon: Properties, models, scaling, and application to biomechanics and motor control. Critical Reviews in Biomedical Engineering, 17(4):359-41 1, 1989; Anderson, F C and Pandy, M G., Static and Dynamic Optimization Solutions for Gait are practically equivalent, Journal of Biomechanics 34, 2001, 153–161, 2001 ; Hungspreugs, P., Thelen, D., Dariush, B., Ng-Thow-Hing, V., Muscle Force Distribution Estimation Using Static Optimization Techniques. Technical Report—Honda R&D Americas, April 2001).

The computed muscle forces are then compared with physiological capacity of the muscle in the muscle capacity module 420. The maximum force limits can be ascertained from the well-studied force-length-velocity relationship of muscle (Zajac 1989, cited above). In addition, the muscle forces with and without the assist torque are compared in order to assess whether the assist torque control has helped (improved efficiency) or hindered the motion. If the assist torque control hinders motion, the muscle forces are adjusted and feasible joint torques are computed (modules 430 and 440 in FIG. 4). A poorly designed assist control would then result in $D\tau' \neq D\tau$, producing a simulated response that would not track the desired response. If the assist torques are well designed, $D\tau'=D\tau$ and the resulting motion would track the desired motion.

Augmentation Device Controller

The inputs to the human augmentation device may include the sensed state variables $q_s$ and/or $\dot{q}_s$, which can be directly measured or estimated. These inputs, denoted by $(q_s, \dot{q}_s)$ represent a subset of the total number of state variables $(q, \dot{q})$ in our human model. In addition to the sensed state variables, measurements may also be used as input to the augmentation device controller. The augmentation device controller output represents the assist torque $\tau_a$, which is then input to the inverse model.

Different control strategies may be used by the human augmentation device controller. For example, gravity compensation control can be used for tasks requiring an increase in potential energy of the total system (human and exoskeleton). Such tasks would include lifting objects, carrying loads, climbing stairs, rising from a chair, etc. A different control strategy, or hybrid control strategies, may be suitable for other tasks such as walking or running. Here, we will present the gravity compensation control algorithm.

By using the Lagrangian, we can assess the total potential energy of the musculoskeletal system. Let U denote the total potential energy stored in the system, $$U = \sum_{i=1}^{n} m_j g^T X_1 \quad (12)$$

The torque at joint i due to gravity can be computed by taking the partial derivative of U with respect to $q_i$, $$D\tau_{gr} = \frac{\partial U}{\partial q_i} = \sum_{j=1}^{n} m_j g^T \frac{\partial X_j}{\partial q_i} \quad (13)$$

where $g^T$ represents the gravitational acceleration vector, and $X_j$ represents the coordinates of the center of mass of segment j. Suppose the knee joint between segment 1 and segment 2 is actuated by an augmentation device and the angle corresponding to $q_2$ (represents $q_s \subset q$) is measurable. The following control law may be used as one algorithm for the augmentation device controller $$D\tau_a = D\tau_{gr} = \frac{\partial U}{\partial q_2} = \sum_{j=1}^{n} m_j g^T \frac{\partial X_j}{\partial q_2} \quad (14)$$

Note that the above control algorithm requires the center of mass positions of all the link segments (denoted by $X_j$). Although $X_j$ can be derived from measurement of joint angles and segment lengths, it may not be feasible to measure all joint angles and all segment lengths. Alternatively, if the vertical component of the ground reaction force under each foot can be measured or estimated, it is possible to derive an iterative "ground up" gravity compensation algorithm which would eliminate the need for access to center of mass of every segment.

Integration of Modules

The block-diagram of the integrated modules as has been presented in the description is shown in FIG. 5. The Augmentation device controller is presumed to have as inputs the sensed states and output the assist torques. The overall framework is very general and enables flexible design of the augmentation device control signals. The details of such designs are easily made by those skilled in the art.

Figure 6:
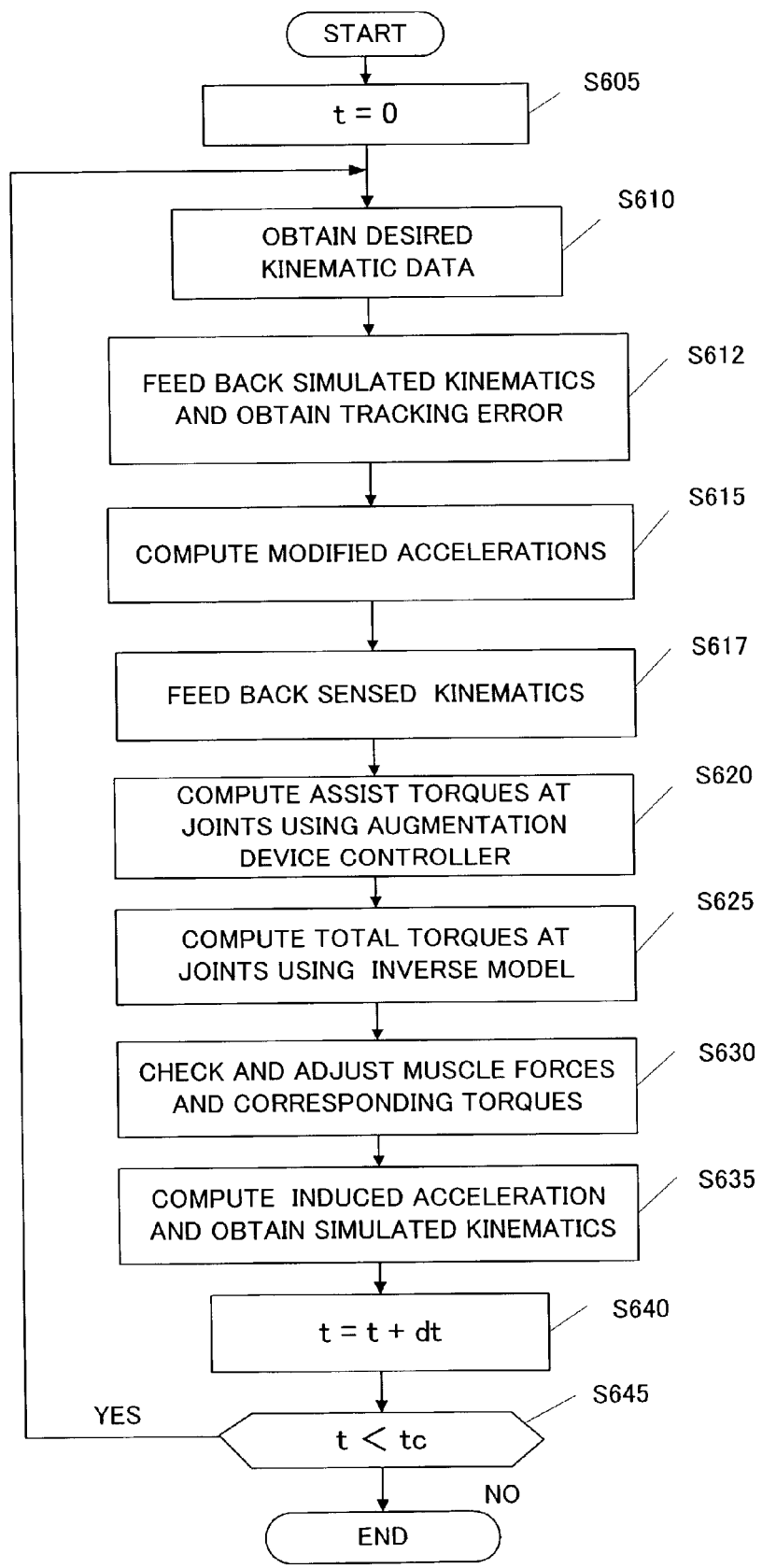
FIG. 6 is a flowchart illustrating a simulation process according to an aspect of the present invention.

FIG. 6 shows a flowchart illustrating a simulation process according to an embodiment of the present invention. At step S605, time t is set to 0. At step S610, desired kinematic data for the combined musculoskeletal and augmentation device system are obtained. The desired kinematic data may be obtained from motion capture data.

At step S612, the simulated kinematic data is fed back to obtain tracking error.

At step S615, modified accelerations $\ddot{q}^*$ are computed using Equation 6.

At step 617, the sensed kinematic data is fed back.

At step S620, assist torques $D\tau_a$ are computed using the augmentation device controller 500.

At step S625, torques $D\tau'$ are computed using Equation 5 (inverse model 300).

At step S630, muscle forces are checked and adjusted to modify the corresponding torques (muscle force and capacity module 400).

At step S635, the induced accelerations $\ddot{q}$ are computed using Equations 3 and 4 and the simulated kinematic data q and $\dot{q}$ are obtained by numerical integration (modules 200, 210 and 220).

At step S640, time t is incremented and at step S645, whether t is less than $t_c$ or not is determined. If t is less than $t_c$, the process returns to step S610. If t is equal to or greater than $t_c$, the process ends.

It should be noted that the above-mentioned equations, modules or functions can be implemented in any kind of computing devices, including general-purpose computers such as personal computers, work stations and main frame computers, and ASICs (Application Specific Integrated Circuits).

In an embodiment a general-purpose computer is employed to implement the invention. The general-purpose computer comprises software representing the above-mentioned equations, modules or functions. The software is preferably contained in computer readable mediums. Computer readable mediums include read only memories, random access memories, hard disks, flexible disks, compact disks and so on.

Simulations

A very simple simulation of the tracking system is carried out to illustrate some of the concepts proposed in the description.

Figure 8:
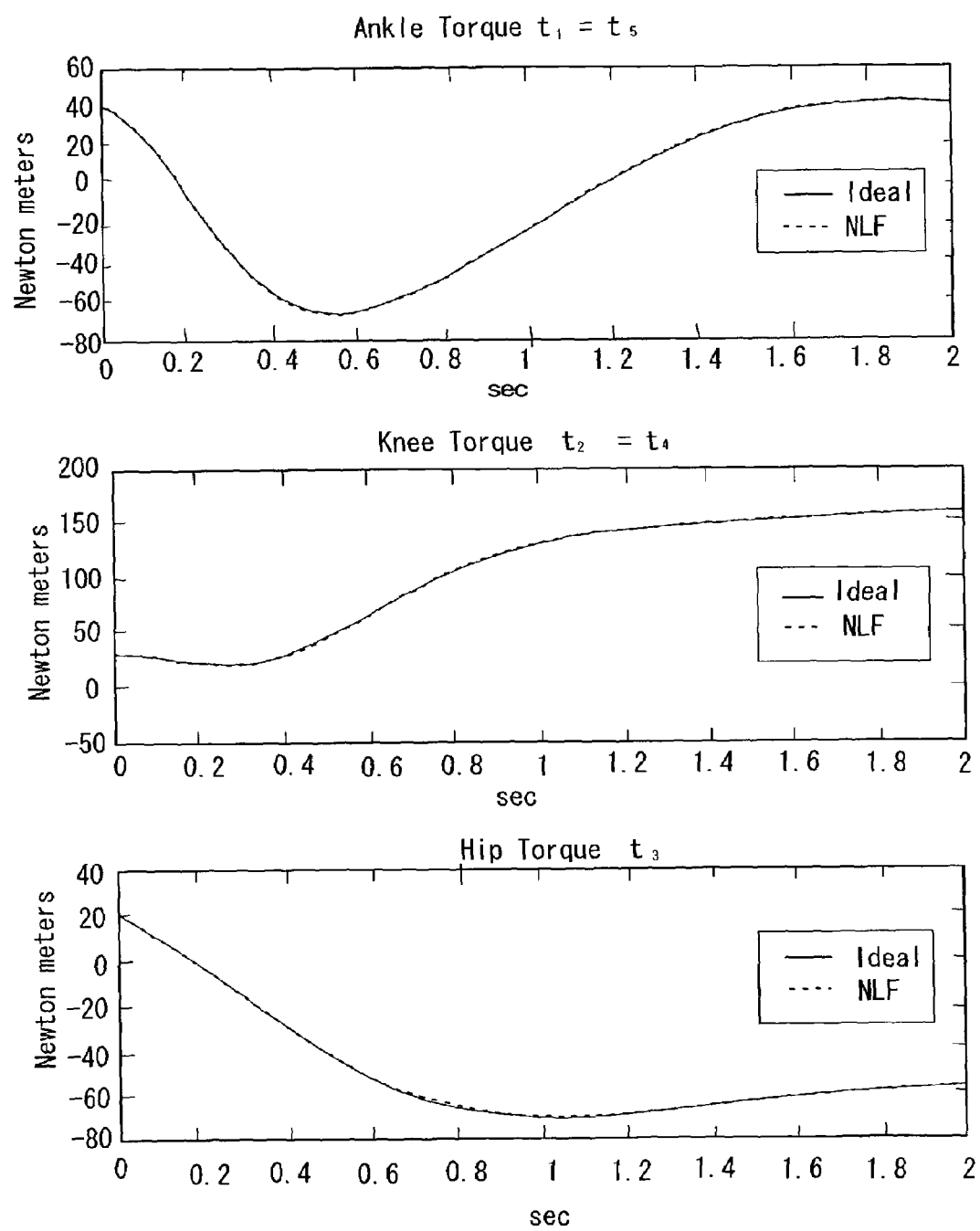
FIG. 8 is a simulation of the joint torques during a squatting maneuver without employing the desired accelerations (a=0), in which the proposed method using nonlinear feedback (NLF) produces nearly identical joint torque estimates as compared to the ground truth (ideal) joint torques obtained by a noise free inverse dynamics computation.
Figure 9:
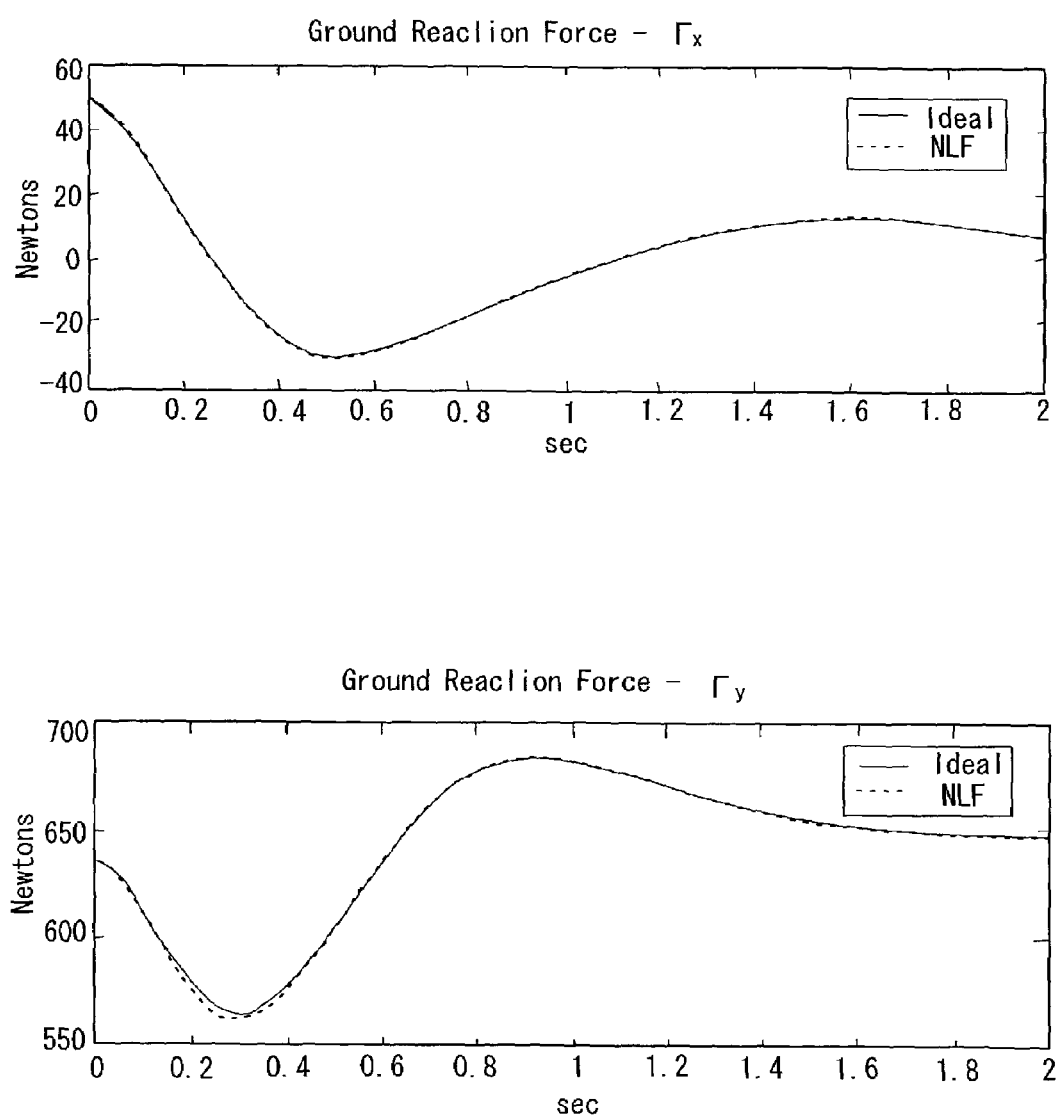
FIG. 9 is a simulation of the horizontal and vertical ground reaction forces during a squatting maneuver without employing the desired accelerations (a=0), in which the proposed method using nonlinear feedback (NLF) produces nearly identical ground reaction estimates as compared to the ground truth (ideal) ground reaction forces obtained by an Iterative Newton Euler inverse dynamics procedure.

A simulation illustrating the tracking characteristics of the proposed method without acceleration estimates of the reference trajectory, is provided. In particular, the double support phase of the biped system during a squatting maneuver was simulated. The results are illustrated in FIGS. 7 to 9.

Figure 7:
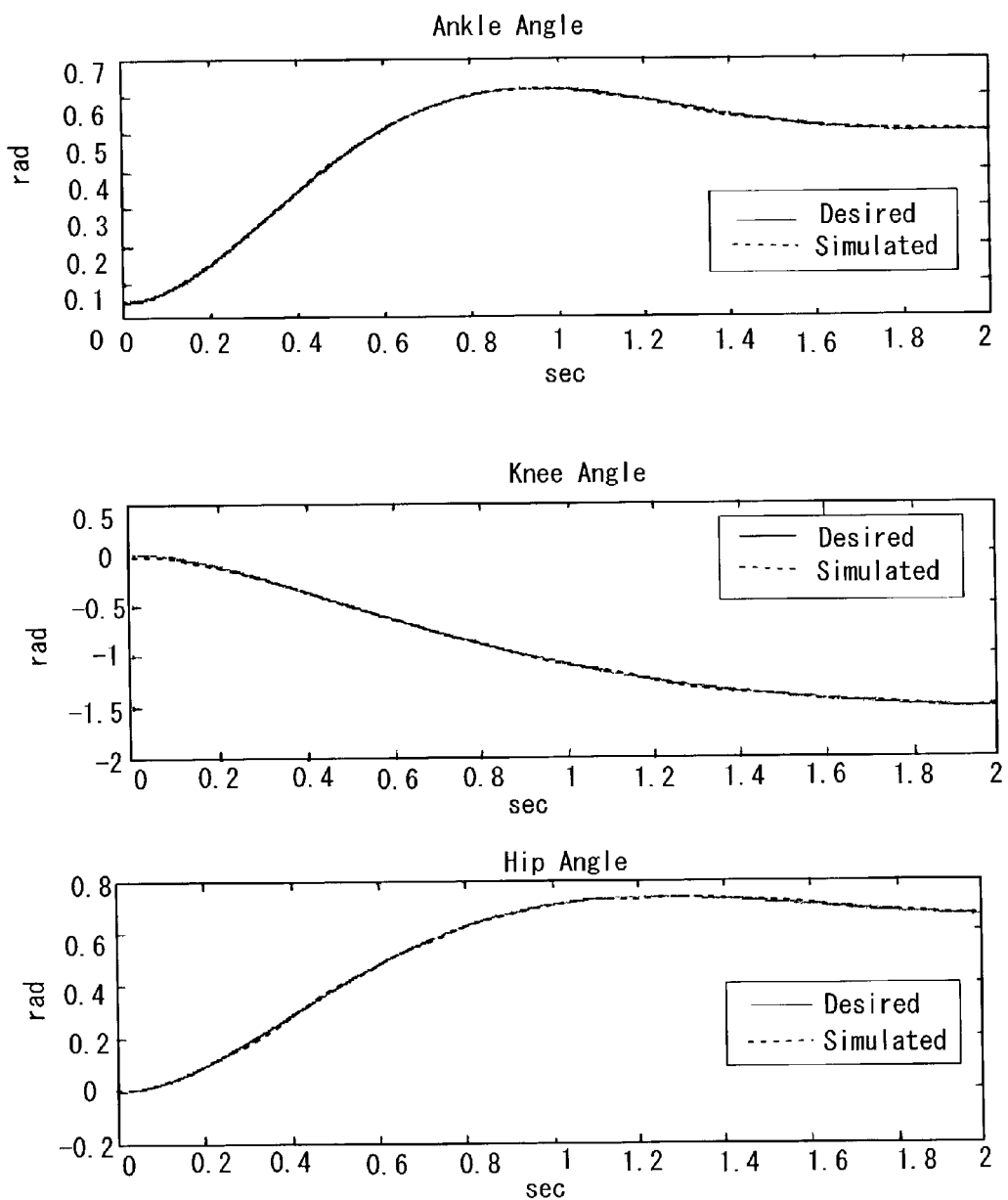
FIG. 7 is a simulation of the joint angles during a squatting maneuver without employing the desired accelerations (a=0), in which nearly perfect tracking of desired kinematic trajectories is illustrated.

In FIG. 7, the desired and simulated joint trajectories illustrate the effectiveness of the tracking procedure. These results were obtained by setting a=0, i.e. no acceleration estimates were used as inputs to the inverse model. The corresponding joint torques and ground reaction forces are depicted in FIG. 8 and FIG. 9, respectively.

It should be noted that those skilled in the art can modify or change the above-mentioned embodiments, without departing from the scope and spirit of the present invention. It should therefore be noted that the disclosed embodiments are not intended to limit the scope of the invention, but only to exemplarily illustrate the invention.

What is claimed is:

1. A simulation system for a combined musculoskeletal and augmentation device system including segments and joints connecting the segments for estimating design of an augmentation device controller, the simulation system comprising:
   a processor;
   a memory operable with the processor for storing:
   a dynamics model of the combined musculoskeletal and augmentation device system receiving computed torques at the joints as inputs and delivering simulated kinematic data of the segments as outputs;
   the augmentation device controller for control of the augmentation device receiving the simulated kinematic data as inputs and delivering assist torques as outputs;
   an inverse dynamics module for the musculoskeletal and augmentation device system receiving the simulated kinematic data, desired kinematic data of the segments and the assist torques as inputs and delivering the computed torques; and a muscle force and muscle capacity module receiving the assist torques as inputs and delivering the computed torques as outputs after checking and adjusting the computed torques, wherein in the muscle force and muscle capacity module muscle forces with and without the assist torques are compared in order to assess whether the assist torque of the augmentation device controller helps or hinders motions, wherein the computed torques are adjusted responsive to the augmentation device controller hindering motion, and computed torques not being adjusted responsive to the augmentation device controller helping motion indicating acceptable estimated design of the augmentation device controller.

2. A simulation system according to claim 1 wherein the muscle force and muscle capacity module deduces muscle forces from the computed torques, compares the muscle forces with maximum force and adjusts a muscle force if the muscle force exceeds a limit, to adjust the corresponding said computed torque.

3. A simulation system according to claim 2 wherein the muscle force and muscle capacity module deduces muscle forces based on a static optimization criterion in which a sum of muscle activation squared is minimized.

4. A simulation system according to claim 1 wherein the inverse dynamics model obtains modified accelerations of kinematic data through non-linear feedback of the simulated kinematic data.

5. A simulation system according to 4, wherein the kinematic data include position data, velocity data and acceleration data and the inverse dynamics model calculates modified accelerations of kinematic data, through non-linear feedback based on error between simulated position data and desired position data or error between simulated velocity data and desired velocity data.

6. A simulation system according to 4, wherein the feedback gains are selected to yield a critically damped response to produce the fastest possible non-oscillatory behavior.

7. A simulation system according to claim 1, further comprising a ground reaction force model receiving the computed torques and the simulated kinematic data as inputs and delivering simulated reaction forces under the segments contacting ground as outputs.

8. A simulation system according to claim 1, wherein the augmentation device controller employs gravity compensation control algorithm in which the augmentation device controller obtains the assist torques to compensate for forces due to gravity and alters the computed torque due to the compensation for gravity.

9. A simulation system according to claim 8, wherein the augmentation device obtains change in the computed torques, due to gravity assist control, using coordinates of a center of mass of the segments.

10. A simulation system according to claim 9, wherein the augmentation device obtains the coordinates of the center of the mass of the segments, from measurements of joint angles and segment lengths.

11. A simulation system according to claim 8, wherein the augmentation device obtains change in the computed torques, due to gravity assist control, using measured reaction forces under feet.

12. A method for simulating a combined musculoskeletal and augmentation device system including segments and joints connecting the segments for estimating assist torques of the augmentation device, the method comprising the steps of:

computing assist torques of the augmentation device, based on simulated kinematic data;

computing torques based on the simulated kinematic data, desired kinematic data of the segments and the assist torques;

checking and adjusting the computed torques; and computing the simulated kinematic data of the segments based on the computed torques at the joints, wherein the step of checking and adjusting the computed torques comprises comparing muscle forces with and without the assist torques in order to assess whether the assist torque of helps or hinders motion, wherein adjusting of the computed torques responsive to the assist torque hindering motion, and the computed torques not being adjusted responsive to the assist torque helping motion indicating good estimation of computed assist torques; and storing the computed torques helping motion.

13. A method according to claim 12, wherein the step of checking and adjusting the computed torques comprises deducing muscle forces from the computed torques, comparing the muscle forces with maximum force limits and adjusting a muscle force if the muscle force exceeds a limit, to adjust the corresponding said computed torque.

14. A method according to claim 13, wherein the step of checking and adjusting the computed torques comprises comparing muscle forces with and without the assist torques in order to assess whether the assist torque helps or hinders motion and designing an assist control law to ensure that the assist torques help the efficiency of motion.

15. A method according to claim 13, wherein muscle forces are deduced, based on a static optimization criterion in which a sum of muscle activation squared is minimized.

16. A method according to claim 12, wherein the step of computing the computed torques comprises computing modified acceleration of kinematic data through non-linear feedback of the modified accelerations kinematic data.

17. A method according to claim 16, wherein the kinematic data include position data, velocity data and acceleration data and computing modified accelerations of kinematic data are computed through non-linear feedback based on desired acceleration data, error between simulated position data and desired position data and error between simulated velocity data and desired velocity data.

18. A method according to claim 16, wherein the kinematic data include position data, velocity data and acceleration data and computing modified accelerations of kinematic data are computed through non-linear feedback based on error between simulated position data and desired position data and error between simulated velocity data and desired velocity data.

19. A method according to claim 12, wherein the step of computing simulated kinematic data of the segments comprises computing reaction forces under the segments contacting ground, based on the computed torques and the simulated kinematic data.

20. A method according to claim 12, wherein the step of computing assist torques of the augmentation device is performed employing gravity compensation control algorithm in which the augmentation device controller obtains the assist torques to compensate for forces due to gravity.

21. A method according to claim 20, wherein change in the computed torques, due to change in gravity assist torque, are computed using coordinates of a center of mass of the segments.

22. A method according to claim 21, wherein the coordinates of the center of the mass of the segments, are obtained from measurements of joint angles and segment lengths.

23. A method according to claim 20, wherein change in the computed torques, due to change in gravity assist torque, are computed using measured reaction forces under feet.

24. A computer readable medium containing a program for simulating a combined musculoskeletal and augmentation device system including segments and joints connecting the segments, the program comprising instructions for:

computing assist torques of the augmentation device, based on simulated kinematic data;

computing torques based on the simulated kinematic data, desired kinematic data of the segments and the assist torques;

checking and adjusting the computed torques;

computing the simulated kinematic data of the segments based on the computed torques at the joints, wherein the step of checking and adjusting the computed torques comprises comparing muscle forces with and without the assist torques in order to assess whether the assist torques help or hinder motion, wherein adjusting of the computed torques responsive to the assist torques hindering motion, and the computed torques not being adjusted responsive to the assist torques helping motion indicating good estimation of computed assist torques; and storing the computed torques helping motion.

* * * * *

UNITED STATES PATENT AND TRADEMARK OFFICE
CERTIFICATE OF CORRECTION

| | | |
|---|---|---|
| PATENT NO. | : 7,251,593 B2 | Page 1 of 1 |
| APPLICATION NO. | : 10/280771 | |
| DATED | : July 31, 2007 | |
| INVENTOR(S) | : Behzad Dariush, Victor Ng-Thow-Hing and Darryl Gerard Thelen | |

It is certified that error appears in the above-identified patent and that said Letters Patent is hereby corrected as shown below:

On cover page, line 12 of the Abstract, please change "assit" to --assist--.

Column 11, Claim 1, Line 11, please change "motions" to --motion--.

Signed and Sealed this

Sixth Day of November, 2007

JON W. DUDAS
*Director of the United States Patent and Trademark Office*